Nov. 20, 1973
B. J. MACHIN
Plant Pat. 3,412
CHRYSANTHEMUM PLANT
Filed Dec. 27, 1971
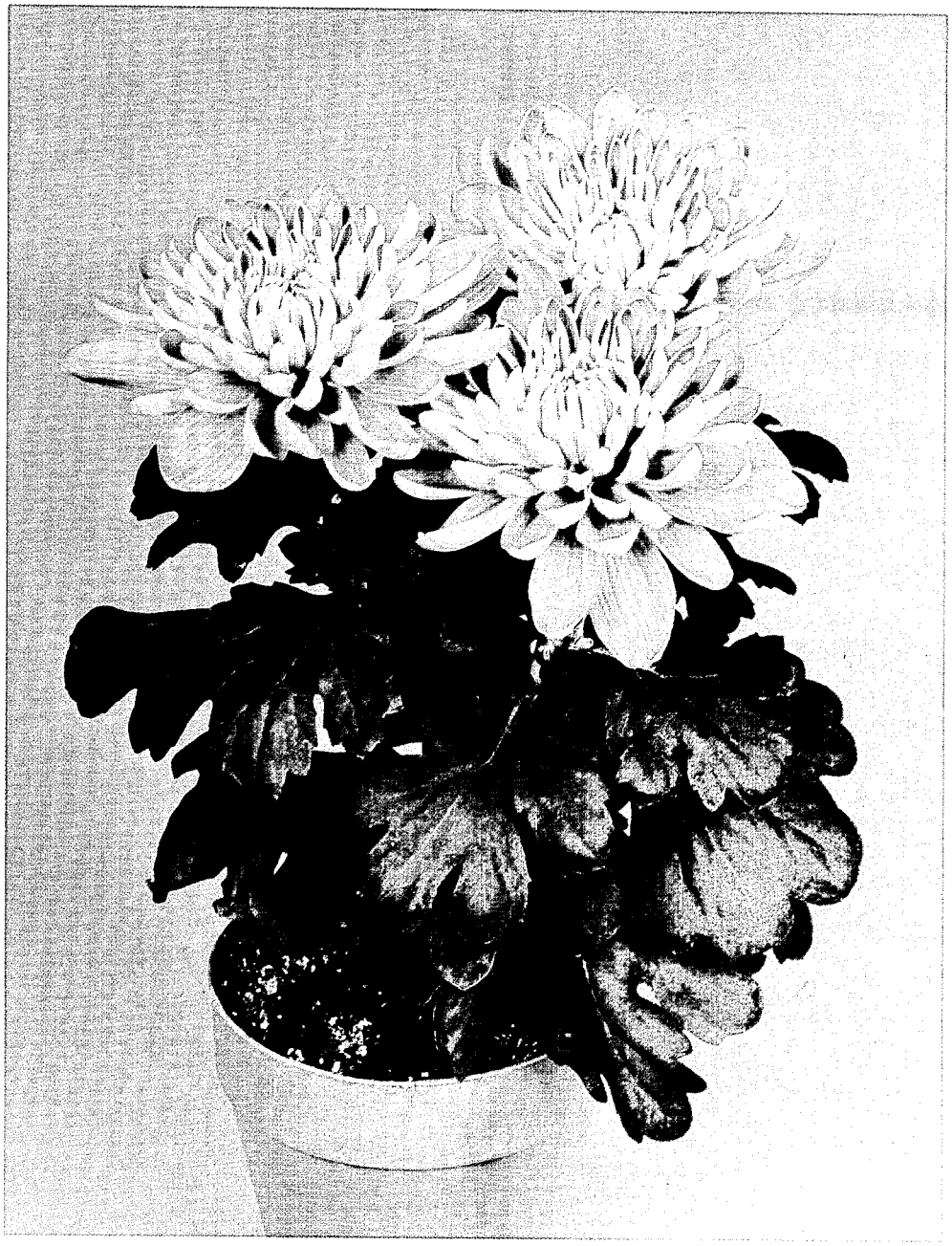

United States Patent Office

Plant Pat. 3,412
Patented Nov. 20, 1973

3,412
CHRYSANTHEMUM PLANT

Barrie John Machin, East Broyle Estate, England, assignor to Frampton's Nurseries Limited, Chichester, Sussex, England Filed Dec. 27, 1971, Ser. No. 212,825
Int. Cl. A01h 5/00
U.S. Cl. Plt.—81 1 Claim This invention relates to a new and distinct variety of *Chrysanthemum morrifolium* Bailey (pot type) known as Deep Louise.

Deep Louise is a sport from a seedling known as Louise (unpatented) originated by me from a cross made in 1966 between the variety Bluebell (unpatented) and the variety Apricot Princess Anne (unpatented), the former being the seed parent, the latter being the pollen parent. The variety Louise resulted from an extensive breeding program with the object of producing improved varieties for year-round pot chrysanthemum production with more uniformity and reduced flowering time as compared with existing varieties.

Deep Louise has the following improved characteristics over Louise:

(1) It has a slightly deeper color.
(2) It retains its color better under high light conditions.

Deep Louise differs from the pollen parent of Louise, in the same way as Louise. In particular:

(1) It is much more responsive and will produce good quality pot plants in 2–3 weeks less growing time round the year.
(2) It is much easier to control the height of the plant and little or no chemical dwarfing measures are required.
(3) Although flowers are smaller, their form is improved and more flowers per plant are obtained.
(4) As compared with Apricot Princess Anne, Deep Louise has flowers which are pink rather than yellow.
(5) Quality of petal is improved in poor winter light conditions.

Deep Louise also differs from the seed parent of Louise in the same way as Louise. In particular, Deep Louise is much more responsive under a wide range of environmental conditions and will produce a flowering pot plant in 2–3 weeks less growing time. Deep Louise has a flower of firmer texture and more incurving shape, a deeper color, a more uniform and slightly earlier response, in winter conditions. The plant is more widely branched and stocky.

Asexual reproduction of this new variety Deep Louise as performed in Sussex, England, by rooting vegetative shoots, shows that the above characteristics are fixed and come true to type through succeeding generations.

The accompanying drawing shows a typical flower of my new variety depicted in color as nearly true as it is reasonably possible to make the same in a color illustration of this character.

The following is a detailed description of the new variety Deep Louise with color terminology in accordance with the Royal Horticultural Society color chart, hereinafter referred to as RHS.

Genus: Chrysanthemum
Species: Morifolium Bailey
Type: Pot
Class: Incurving decorative
Breeding: Original variety Louise resulted from a cross between the variety Bluebell and Apricot Princess Anne, the former being the seed parent, the latter being the pollen parent. This cross was made in 1966 at Frampton's Nurseries Ltd., Forbridge Nursery, Chichester, Sussex, England. The deep sport known as Deep Louise was found by me in June 1969 at the above address.
Propagation: Holds its distinguishing characteristics through succeeding propagations by rooting vegetative shoots.
Flower: When grown and observed in Sussex, England, in 3½ inch pots and pinched, up to six flowers per plant are formed. When five plants are planted per five inch pot, 4 to 5 flowers are borne on each plant.
Bloom:
*Size.*—Average diameter is 8 cm. when fully open.
*Petalage.*—Decorative with approximately 150 to 200 ray petals and 10 to 20 disc petals.
*Form.*—Incurving decorative.
*Petals.*—Medium length, broad, overlapping, blunt, flat and of thick texture.
Color of open bloom: Inner face of fully expanded petal RHS 70C. Outer face of fully expanded petal RHS 62D. Inner face of young petal RHS 70C. Outer face of young petal RHS 62D.
Response group: 8 weeks.
Temperature tolerance: 55–60° F. at night.
Plant: Stocky, well branch habit of growth.
Foliage: Medium quality. Average internode length 1½ to 2 cm. Medium size. Color RHS 144A. Medium texture.
Stem: Thick and strong. Color RHS 144C at flowering.

I claim:

1. A new and distinct variety of *Chrysanthemum morrifolium* Bailey (pot type), substantially as herein shown and described, having incurving decorative reddish purple petals characterized particularly as to novelty by the fact that the inner faces of its petals have a color substantially as deep as RHS 70C, and by improved color retention under high light conditions.

No references cited.

ROBERT E. BAGWILL, Primary Examiner